(12) United States Patent
Tang et al.

(10) Patent No.: US 11,644,400 B2
(45) Date of Patent: May 9, 2023

(54) AIR PRESSURE-MACHINE VISION BASED SYSTEM AND METHOD FOR MEASURING RHEOLOGICAL PROPERTY OF VISCOELASTIC MATERIAL

(71) Applicant: China Agricultural University, Beijing (CN)

(72) Inventors: Xiuying Tang, Beijing (CN); Xiuzhi Luo, Beijing (CN); Qinming Sun, Beijing (CN); Ke He, Beijing (CN)

(73) Assignee: China Agricultural University, Beijing (CN)

(*) Notice: Subject to any disclaimer, the term of this patent is extended or adjusted under 35 U.S.C. 154(b) by 0 days.

(21) Appl. No.: 17/901,863

(22) Filed: Sep. 2, 2022

(65) Prior Publication Data

US 2023/0063766 A1 Mar. 2, 2023

(30) Foreign Application Priority Data

Sep. 2, 2021 (CN) .......................... 202111023170.8

(51) Int. Cl.
| | |
|---|---|
| *G01N 11/00* | (2006.01) |
| *B01L 9/02* | (2006.01) |
| *G01N 33/02* | (2006.01) |

(52) U.S. Cl.
CPC ............ *G01N 11/00* (2013.01); *B01L 9/02* (2013.01); *G01N 33/02* (2013.01); *G01N 2011/008* (2013.01)

(58) Field of Classification Search
CPC .. G01N 11/00; G01N 33/02; G01N 2011/008; B01L 9/00
See application file for complete search history.

(56) References Cited

U.S. PATENT DOCUMENTS 9,759,642 B2 * 9/2017 Newman ................ G01N 33/26

FOREIGN PATENT DOCUMENTS

| CN | 101430267 A | 5/2009 |
|---|---|---|
| CN | 108956376 A | 12/2018 |

(Continued)

OTHER PUBLICATIONS

English translation of CN108956376 accessed from iq.ip.com Dec. 12, 2022.*

(Continued)

*Primary Examiner* — David Z Huang
*Assistant Examiner* — Jean F Morello
(74) *Attorney, Agent, or Firm* — Bayramoglu Law Offices LLC

(57) ABSTRACT

An air pressure-machine vision based system for measuring a rheological property of a viscoelastic material includes a machine body, a lifting experiment table system, an air pressure generation control system, an image collection system, and a controlling and information processing system, where the lifting experiment table system, the air pressure generation control system, the image collection system and the controlling and information processing system are mounted on the machine body; the lifting experiment table system includes a lifting table stepping motor, an L-shaped lifting table and a lifting table motor driver, and the lifting table motor driver is connected to the lifting table stepping motor and configured to drive the lifting table stepping motor; and the lifting table stepping motor is connected to the L-shaped lifting table and configured to control lifting of the L-shaped lifting table.

2 Claims, 9 Drawing Sheets

(56) References Cited

FOREIGN PATENT DOCUMENTS

| CN | 108958306 | A |   | 12/2018 |
|----|-----------|---|---|---------|
| CN | 213121641 | U | * | 5/2021  |
| CN | 113008735 | A |   | 6/2021  |
| JP | 2005121614 | A | * | 5/2005 |
| WO | 2014182317 | A1 |  | 11/2014 |

OTHER PUBLICATIONS

English translation of JP2005121614 accessed from iq.ip.com Dec. 12, 2022.*

English translation of CN213121641 accessed from iq.ip.com Dec. 12, 2022.*

Xu Hubo, et al., Evaluation of Chicken Tenderness Based on Controlled Air-flow Laser Detection Technique, Journal of Agricultural Machinery, 2020, pp. 457-465, vol. 51, No. 2.

Niveditha Asaithambi, et al., Evaluation of bread dough aeration during kneading by an air-jet impulse system, Journal of Food Engineering, 2020, pp. 1-10, vol. 278, 109931.

* cited by examiner

AIR PRESSURE-MACHINE VISION BASED SYSTEM AND METHOD FOR MEASURING RHEOLOGICAL PROPERTY OF VISCOELASTIC MATERIAL

CROSS REFERENCE TO THE RELATED APPLICATIONS

This application is based upon and claims priority to Chinese Patent Application No. 202111023170.8, filed on Sep. 2, 2021, the entire content of which is incorporated herein by reference.

TECHNICAL FIELD

The present disclosure relates to the field of measurement, in particular to an air pressure-machine vision based system and method for measuring a rheological property of a viscoelastic material.

BACKGROUND

Viscoelastic materials include viscoelastic food and some viscoelastic soft industrial materials, so a rheological property of the food can effectively reflect a processing property of the food and a change process of the quality of the food in a storage process, the research on the rheological property of the food has important significance for nondestructive detection of the food, and the rheological properties of some viscoelastic soft industrial materials can also be studied as a way of detecting the internal quality of the materials. In current rheological property measuring methods, an instrumentation method is commonly used, and main instruments used include a texture analyzer, a rheometer and a dynamic thermodynamic analyzer. Although the instruments have high measurement precision, the instruments are not flexible enough during tests, and will cause pollution among different test samples. As a viscoelasticity measuring means, an air pressure-laser technology has been used for a series of researches in medical and agricultural product nondestructive detection. However, as a measuring means, the air pressure-laser technology has the following problems: firstly, a single-point laser is inaccurate for measurement of deformation of the viscoelastic material, since a distance measured by the single-point laser may not be a maximum value of a deformation depth of a viscoelastic material sample under the action of the air pressure force; and secondly, deformation information obtained by the single-point laser is single, which cannot reflect an overall space rheological feature of the material in a creep process under the air pressure action well. On account of the problems, the quality property measurement of the viscoelasticity of the material is single, and the measurement accuracy is inaccurate.

Therefore, mainly for soft materials with viscoelasticity, and particularly for meat products, part of rice and flour products and some soft viscoelastic industrial materials, the present disclosure provides an air pressure-machine vision based system for measuring a rheological property of a viscoelastic material, which can measure the rheological property of the viscoelastic material, so as to detect an overall visual deformation process of the material.

SUMMARY

The objective of the present disclosure is achieved by using the following technical solution:

An air pressure-machine vision based system for measuring a rheological property of a viscoelastic material includes a machine body, a lifting experiment table system, an air pressure generation control system, an image collection system, and a controlling and information processing system, where the lifting experiment table system, the air pressure generation control system, the image collection system and the controlling and information processing system are mounted on the machine body; the lifting experiment table system includes a lifting table stepping motor, an L-shaped lifting table and a lifting table motor driver, and the lifting table motor driver is connected to the lifting table stepping motor and configured to drive the lifting table stepping motor; and the lifting table stepping motor is connected to the L-shaped lifting table and configured to control lifting of the L-shaped lifting table.

According to the air pressure-machine vision based system for measuring a rheological property of a viscoelastic material, the air pressure generation control system includes an air compressor, a pressure regulating valve, a two-stage air filter, an electrical proportional valve, a two-position five-way double-head pneumatic solenoid valve, a first air chamber and a second air chamber, where the first air chamber and the second air chamber are mounted on the L-shaped lifting table separately, the first air chamber is mounted on a vertical plate of the L-shaped lifting table, the second air chamber is mounted on a bottom plate of the L-shaped lifting table, and the first air chamber is mounted at a second air chamber upper portion.

According to the air pressure-machine vision based system for measuring a rheological property of a viscoelastic material, an air outlet of the air compressor is connected to an air inlet of the pressure regulating valve, an air outlet of the pressure regulating valve is connected to an air inlet of the two-stage air filter, an air outlet of the two-stage air filter is connected to an air inlet of the electrical proportional valve, an air outlet of the electrical proportional valve is connected to an air inlet of the two-position five-way double-head pneumatic solenoid valve, two air outlets of the two-position five-way double-head pneumatic solenoid valve are connected to air inlets of the first air chamber and the second air chamber respectively, an air outlet of the first air chamber is connected to a first nozzle, and an air outlet of the second air chamber is connected to a second nozzle.

According to the air pressure-machine vision based system for measuring a rheological property of a viscoelastic material, the first air chamber has a shape of an octagonal prism, one surface of the octagonal prism is fixed to a vertical surface of the L-shaped lifting table, and the first nozzle is mounted on a surface adjacent to a lower side of a surface opposite the surface; the first air chamber includes an air chamber upper portion and an air chamber lower portion, the air chamber upper portion is connected to the air chamber lower portion by means of screws, a circle of sealing groove is provided in the air chamber upper portion, a circle of flange is arranged on the air chamber lower portion, and the flange is embedded into the sealing groove and abuts against a rubber gasket preset in the sealing groove to achieve sealing so as to prevent air leakage; and an air inlet is provided in a side surface of the air chamber upper portion, an air outlet is provided in a bottom cover of the air chamber lower portion and is in threaded connection to the first nozzle, and a joint is sealed by means of cold-setting adhesive.

According to the air pressure-machine vision based system for measuring a rheological property of a viscoelastic material, a side cover on the first air chamber upper portion is connected to a side plate of the L-shaped lifting table by means of bolts, the first nozzle is mounted on the bottom cover on the first air chamber lower portion, and the first nozzle inclines downwards to face a top surface of a lower portion of the second air chamber.

According to the air pressure-machine vision based system for measuring a rheological property of a viscoelastic material, an inner cavity of the first nozzle is provided with a connecting section, a converging section and a diverting section from top to bottom sequentially; an outer wall where the diverting section is located is provided with external threads and is connected to an air chamber main body by means of the threads, cold-setting adhesive seals the connecting section of the nozzle, the connecting section is cylindrical, the converging section is conical and has an upper portion larger than a lower portion, the diverting section is cylindrical, a length ratio of the converging section to the diverting section is not greater than 1:1.3, and a ratio of a length of the diverting section to a diameter of an air outlet hole in the diverting section is not less than 3:1.

According to the air pressure-machine vision based system for measuring a rheological property of a viscoelastic material, the second air chamber has a cubic structure, the lower portion of the second air chamber is fixed to the bottom plate of the L-shaped lifting table by means of screws, the second air chamber includes an air chamber upper portion and an air chamber lower portion from top to bottom sequentially, the air chamber upper portion is connected to the air chamber lower portion by means of screws, a circle of sealing groove is provided in the air chamber lower portion, a circle of flange is arranged on the air chamber upper portion, the flange is embedded into the sealing groove and abuts against a rubber gasket preset in the sealing groove, the air inlet is provided in a side surface of the air chamber upper portion, the air outlet is provided in the middle of a top surface of the air chamber upper portion and used for mounting the second nozzle, and a groove and a threaded hole are provided in a surface of the air chamber upper portion for mounting and fixing a sample fixture.

The air pressure-machine vision based system for measuring a rheological property of a viscoelastic material further includes a sample fixing clamp, the circle of groove and the two threaded holes are provided in the surface of the second air chamber upper portion, the air outlet is located in a center of the groove in the second air chamber upper portion, and the second nozzle is mounted at the air outlet; the sample fixing clamp includes a base and a pressing nut, a base body is of a hollow cylinder shape, and a threaded hole is provided in a surface of the base and used for mounting and fixing the base on the surface of the second air chamber upper portion by means of a screw; a lower portion of the base body protrudes outwards to form a circle of flange, a portion, below the flange, of the base body is embedded into the groove in the surface of the second air chamber upper portion, an upper portion of the base body is provided with external threads, the pressing nut is provided with internal threads corresponding to the external threads, and the pressing nut is connected to the base by means of threads; a circle of boss is arranged on a lower portion in a cavity of the base body, four positioning plates are arranged on an upper portion of the boss and are oppositely arranged pairwise, side edges, away from a cavity wall, of the positioning plates are straight edges, and the side edges between two opposite positioning plates are parallel to each other; and the pressing nut is a hollow nut, and an inner cavity of the pressing nut extends downwards to form a circle of rib for fixing an experimental sample.

According to the air pressure-machine vision based system for measuring a rheological property of a viscoelastic material, the image collection system includes a camera, the controlling and information processing system includes a mobile computer and an A/D conversion module, and the mobile computer is connected to the camera; the A/D conversion module is connected to the two-position five-way double-head pneumatic solenoid valve and is used for controlling on-off of the air outlets, connected to the two air chambers respectively, of the two-position five-way double-head pneumatic solenoid valve; during working, a viscoelastic material sheet is flatly laid on the boss, the pressing nut is screwed from top to bottom, and the inner cavity of the pressing nut extends downwards to form a circle of rib to act on the surface of the viscoelastic material sample, such that the viscoelastic material sheet is fixed, and air pressure acts on an upper surface or a lower surface of the viscoelastic material; and the camera collects continuous change images of a concave or convex process of the viscoelastic material and sends the images to the mobile computer.

According to the air pressure-machine vision based system for measuring a rheological property of a viscoelastic material, the camera is a two-dimensional camera, and the mobile computer receives image data collected by the two-dimensional camera to perform the following steps:

step 1. calling an Opencv two-dimensional image processing library, performing binarization processing on the obtained image, performing negation operation to obtain a background segmented mask image, and using the mask to remove a viscoelastic material background by means of the following operational formula:

$$I_{mask} = I * I_{temp} \quad (1)$$

where in the formula, $I_{mask}$ is a background segmented image obtained by preprocessing, and $I_{temp}$ is a mask;

step 2. extracting a gray level image of an RGB image of the viscoelastic material sample subject to background segmentation, and quantifying the gray level image at the gray level;

step 3. selecting parameters, specifically, (1) selecting, by taking a pixel point to be computed as a center, a size of a matrix to be computed; (2) setting a distance between the selected pixel point and another point deviating from the selected pixel point as step distance d; and (3) selecting a direction $\varphi^\circ$, where selected directions include 0°, 45°, 900 and 135°; and step 4. extracting a rheological process deformation feature of the image of the viscoelastic material sample, where feature $f_1$ is used for representing similarity, in a transverse direction and a longitudinal direction, obtained after statistics is performed on the condition that two pixels which are kept at a certain distance in the image of the material sample have certain gray levels respectively;

feature $f_2$ is used for representing grooves on the surface of the viscoelastic material;

feature $f_3$ is used for representing a uniformity degree of gray level distribution and a thickness degree of texture of the image of the viscoelastic material sample;

feature $f_4$ is used for representing local texture change between different regions of the image of the viscoelastic material sample; and feature $f_5$ is used for representing a degree of regularity of the texture of the image of the viscoelastic material sample.

According to the air pressure-machine vision based system for measuring a rheological property of a viscoelastic material, where mathematical formulas for extracting the five texture features $f_1$, $f_2$, $f_3$, $f_4$, $f_5$ of the image of the material sample are as follows:

feature $f_1$:

$$f_1 = \frac{\sum_{i=0}^{N-1}\sum_{j=0}^{N-1}[i \times j \times p(i,j) - \mu_x\mu_y]}{\sigma_x^2\sigma_y^2} \quad (2)$$

feature $f_2$:

$$f_2 = \sum_{i=0}^{N-1}\sum_{j=0}^{N-1}[(i-j)^2 p(i,j)] \quad (3)$$

feature $f_3$:

$$f_3 = \sum_{i=0}^{N-1}\sum_{j=0}^{N-1} p^2(i,j) \quad (4)$$

feature $f_4$:

$$f_4 = \sum_{i=0}^{N-1}\sum_{j=0}^{N-1}\frac{p(i,j)}{1+(i-j)^2} \quad (5)$$

feature $f_5$:

$$f_5 = -\sum_{i=1}^{N-1}\sum_{j=1}^{N-1} p(i,j)\log p(i,j) \quad (6)$$

in the formula $$\mu_x = \sum_{i=0}^{N-1} i \sum_{j=0}^{N-1} p(i,j); \quad \mu_y = \sum_{i=0}^{N-1} j \sum_{j=0}^{N-1} p(i,j);$$

$$\sigma_x^2 = \sum_{i=0}^{N-1}(i-\mu_x)^2 \sum_{j=0}^{N-1} p(i,j); \quad \sigma_y^2 = \sum_{i=0}^{N-1}(i-\mu_y)^2 \sum_{j=0}^{N-1} p(i,j)$$

in the formula:

$$p(i,j) = \frac{p_{ij}}{\sum_{i=0}^{N-1}\sum_{j=0}^{N-1} p_{ij}};$$

p in the formula is an N*N two-dimensional matrix; p(i, j) is a probability of co-occurrence of two gray values i and j of a reference point (x, y) and an offset point (x+d, y+d), with a given distance d and a given direction $\varphi^0$, on a straight line with a direction $\varphi^0$, the gray value of the reference point (x, y) is i, and the gray value of the offset point (x+d, y+d) is j; $p_{ij}$ is the number of times that a reference gray pixel value i appears in a pixel pair with a gray pixel value j with a distance d and a direction $\varphi^0$; N is a gray level of one image; and x and y are horizontal axis coordinates of the pixel point respectively.

According to the air pressure-machine vision based system for measuring a rheological property of a viscoelastic material, the camera is a three-dimensional structured light camera, and after the mobile computer receives image data collected by the three-dimensional structured light camera, the following steps are executed: calling, by the mobile computer, a point cloud processing library (PCL), and performing extraction and display of feature information of three-dimensional structural deformation on an obtained point cloud image.

Specifically, (1) extracting a plane projection area of a deformation convex or concave region of a three-dimensional structure, firstly extracting an interested region of obtained deformation convex or concave point cloud of viscoelastic food, performing denoising and downsampling processing to reduce a data size and noise so as to obtain a deformed overall contour, projecting point cloud data subject to downsampling processing to plane XOY, plane XOZ and plane YOZ, dividing three adjacent points into a triangle in three coordinate planes respectively to establish a triangle patch index, and traversing and respectively accumulating and computing areas $S_{xoy}$, $S_{xoz}$, and $S_{yoz}$ projected to plane XOY, plane XOZ and plane YOZ, where $$S_{xoy}, S_{xoz}, S_{yoz} = \Sigma_{i=0}^{n} s_i \quad (1), \text{where:}$$

$S_i$ is an area of each projected triangle on the plane, and is computed by means of a formula:

$$S_i = \sqrt{l_i(l_i-a_i)(l_i-b_i)(l_i-c_i)} \quad (2)$$

where i refers to a patch index number, $l_i$, refers to ½ of a perimeter of the triangle, $a_i$, $b_i$ and $c_i$ refer to side lengths of the triangle, and n refers to a total patch number;

(2) extracting a volume of the deformation convex or concave region of the three-dimensional structure, firstly projecting obtained deformation convex or concave point cloud to plane XOY, performing mesh division on plane points by means of cubic spline interpolation processing, computing an average value hi of a difference between an area of each mesh and an elevation parameter of an original point cloud, and traversing the entire plane, and performing accumulation to obtain a volume V of the concave deformation region, that is, $$V = \sum_{i=0}^{n} S_i h_i; \quad (3)$$

(3) computing a surface area of a triangular mesh curved surface of the deformation convex or concave region of the three-dimensional structure, specifically, performing curved surface interpolation fitting on obtained deformation convex or concave region point cloud, removing discrete points, selecting a sample triangular patch from uniformly distributed scattered points subject to downsampling processing as an initial curved surface, taking the triangular patch as a space region growth point, continuously extending a boundary of the curved surface around to finally form a complete triangular mesh curved surface, and obtaining a triangular mesh curved surface model according to a topological connection relation of three points in the plane; where each patch includes an index of the original point cloud, the entire curved surface mesh is traversed, and the areas of the triangles are accumulated to obtain a point cloud area Sb of a space viscoelastic sample, $$S_b = \sum_{j=0}^{n} s_j, \quad (4)$$

where j refers to a patch index number, $s_j$ refers to a triangle area (computed in the same way as formula 2), and n refers to a total patch number; and (4) extracting a height or depth of the deformation convex or concave region of the three-dimensional structure, using a minimum bounding box algorithm to enclose all scattered points of the deformation convex or concave region of the three-dimensional structure into a minimum cuboid, where the minimum cuboid has a minimum volume, and obtaining eight vertex coordinates of a bounding box of the minimum cuboid by means of computation, where the height or depth H of the deformed region is a vertical distance of the bounding box and may be expressed as:

$$H = \sqrt{(x_1-x_5)^2 + (y_1-y_5)^2 + (z_1-z_5)^2}$$

where $x_1$, $y_1$ and $z_1$ are coordinates of a first vertex of an upper plane of the bounding box, $x_5$, $y_5$ and $z_5$ are coordinates of a fifth vertex of a lower plane of the bounding box, and the first vertex and a second vertex are located on one edge.

BRIEF DESCRIPTION OF THE DRAWINGS

FIGS. 7A-7D show structural schematic diagrams of a base and a presser nut which constitute a viscoelastic sample fixing clamp, wherein FIG. 7A is a top view of the base, a component of the fixing clamp; FIG. 7B is a sectional-structure schematic diagram of the base; FIG. 7C is a side view of a pressing nut; and FIG. 7D is a sectional-structure schematic diagram of the pressing nut;

FIGS. 8A-8E show schematic diagrams of a combination of a pressing nut and a base of a viscoelastic sample fixing clamp, wherein FIG. 8A is a top view of the viscoelastic sample fixing clamp; FIG. 8B is a side view of the viscoelastic sample fixing clamp; FIG. 8C is a sectional-structure schematic diagram of the top view and the side view of the viscoelastic sample fixing clamp; FIG. 8D is left and right equiangular axis side diagrams; and FIG. 8E is left and right equiangular axis side sectional-structure schematic diagrams; and FIGS. 9A-9B show schematic diagrams of a layout structure of a combination of a fixing clamp and a second air chamber, wherein FIG. 9A is a front view of the combination of the second air chamber and the fixing clamp; and FIG. 9B is a sectional-structure schematic diagram of the front view of the combination of the second air chamber and the fixing clamp.

1. foot, 2. second air chamber, 3. first air chamber, 4. lifting table stepping motor, 5. annular LED light source, 6. proportional valve, 7. camera (two-dimensional camera or three-dimensional camera), 8. power transformer, 9. two-position five-way double-head pneumatic solenoid valve, 10. L-shaped connector, 11. middle partition plate, 12. pressure gauge, 13. pressure regulating valve, 14. Two-stage air filter, 15. motor driver, 16. A/D conversion module, 17. isolation box, 18, 19. USB wiring hole, 20. power switch and power plug, 21. light source switch, 22. reset switch, 23. first nozzle, 24. L-shaped lifting table, 25. second nozzle, 26. fixing clamp base, 27. fixing clamp pressing nut, 28. thread, 29. viscoelastic material sample, 30. air outlet of first air chamber, 31. rubber gasket, 32. first air chamber upper portion, 33. first air chamber lower portion, 34. air inlet of first air chamber, 35. diverting section of first nozzle, 36. converging section of first nozzle, 37. connecting section of first nozzle, 38. air inlet of second air chamber, 39. second air chamber upper portion, 40. second air chamber lower portion, 41. air outlet of second air chamber, 42. groove of surface of second air chamber upper portion, 43. a circle of flange at lower portion of fixing clamp base, 44. positioning plate, 45. sample accommodating boss, 46. threaded hole, and 47, solid rib.

DETAILED DESCRIPTION OF THE EMBODIMENTS

A specific implementation mode of the present disclosure is described in detail below in conjunction with FIGS. 1-9B.

Figure 1:
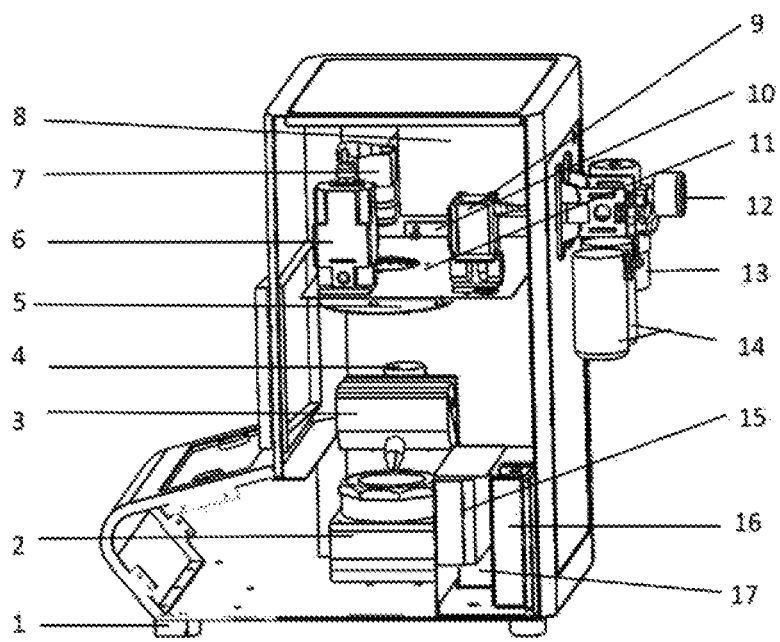
FIG. 1 is a schematic diagram of a right sectional structure of an air pressure-machine vision based system for measuring a rheological property of a viscoelastic material in the present disclosure.
Figure 2:
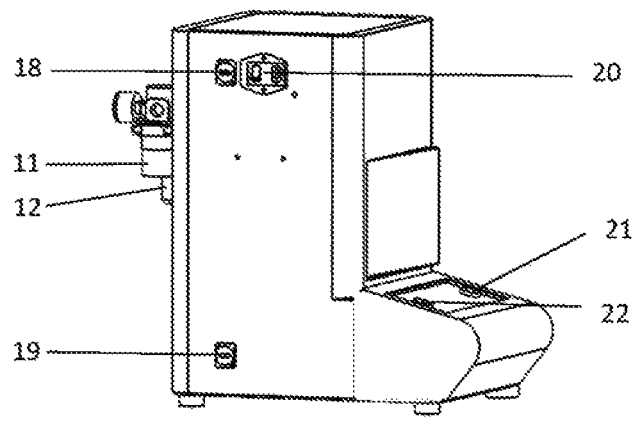
FIG. 2 is a schematic diagram of a left structure of an air pressure-machine vision based system for measuring a rheological property of a viscoelastic material in the present disclosure.

As shown in FIGS. 1 and 2, an air pressure-machine vision based system for measuring a rheological property of a viscoelastic material includes a machine body, a lifting experiment table system, an air pressure generation control system, an image collection system, an illumination control system, and a controlling and information processing system. The lifting experiment table system, the air pressure generation control system, the image collection system and the controlling and information processing system are mounted on the machine body.

The machine body includes a top plate, a side plate, a bottom plate, a machine box main body and a partition plate; and the machine box main body is of a frame type structure, and the top plate is connected to the machine box main body by means of a screw. The side plate is connected to the machine box main body by means of an L-shaped connector 10, a screw and a nut. The bottom plate is connected to the machine box main body by means of an L-shaped connector 10 and a screw. A back plate is connected to the machine box main body by means of a screw. The middle partition plate 11 is connected to the machine box main body by means of an L-shaped connector 10 and a screw. Foots 1 are arranged at four corners of a bottom of the machine body respectively.

Figure 3A:
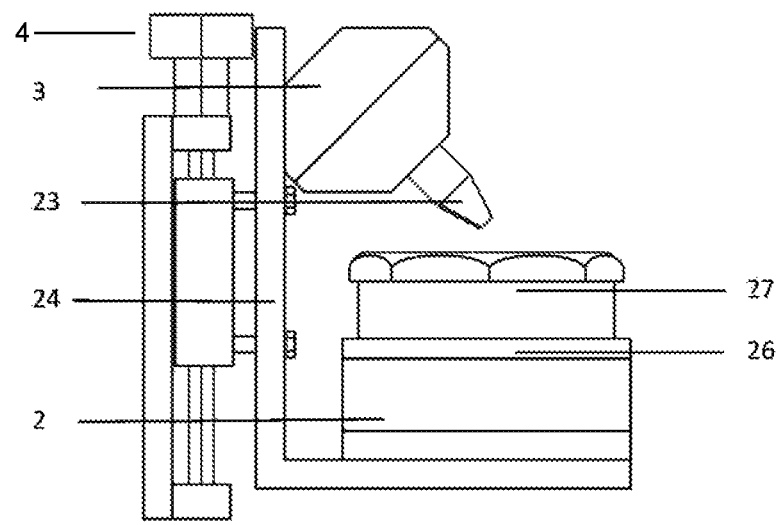
FIGS. 3A-3C are schematic diagrams of layout structures of two air chambers, two nozzles, a fixing clamp and a lifting table in the present disclosure.
Figure 3B:
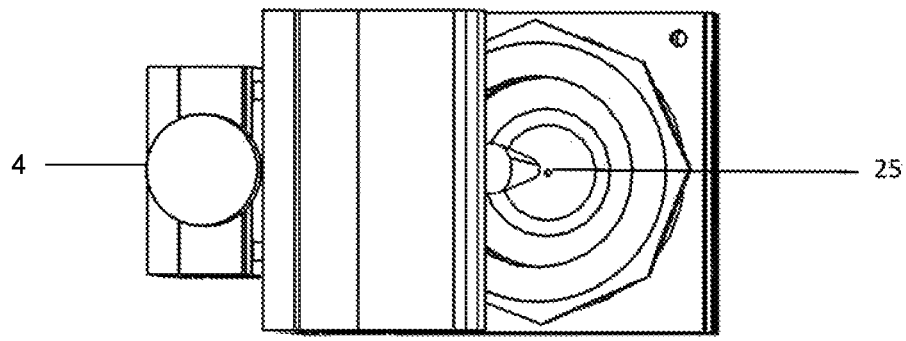
Figure 3C:
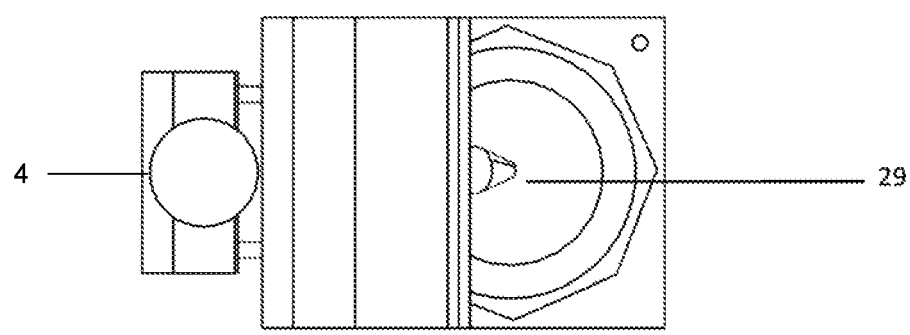

As shown in FIG. 3, the lifting experiment table system includes a lifting table stepping motor 4, an L-shaped lifting table 24 and a lifting table motor driver 15, and the lifting table motor driver 15 is connected to the lifting table stepping motor 4 and configured to drive the lifting table stepping motor 4; and the lifting table stepping motor 4 is connected to the L-shaped lifting table 24 and configured to control lifting of the L-shaped lifting table 24.

The air pressure generation control system includes an air compressor, a pressure regulating valve 13, a two-stage air filter 14, an electrical proportional valve 6, a two-position five-way double-head pneumatic solenoid valve 9, a first air chamber 3, a second air chamber 2, a first nozzle 23 and a second nozzle 25, where the first air chamber 3 and the second air chamber 2 are mounted on the L-shaped lifting table 24 separately, the first air chamber 3 is mounted on a vertical plate of the L-shaped lifting table 24, the second air chamber 2 is mounted on a bottom plate of the L-shaped lifting table, and the first air chamber 3 is mounted at an upper portion of the second air chamber 2. An air outlet of the air compressor is connected to an air inlet of the pressure regulating valve 13, an air outlet of the pressure regulating valve 13 is connected to an air inlet of the two-stage air filter 14, an air outlet of the two-stage air filter 14 is connected to an air inlet of the electrical proportional valve 6, an air outlet of the electrical proportional valve 6 is connected to an air inlet of the two-position five-way double-head pneumatic solenoid valve 9, two air outlets of the two-position five-way double-head pneumatic solenoid valve 9 are connected to air inlets of the first air chamber 3 and the second air chamber 2 respectively, an air outlet of the first air chamber 3 is connected to the first nozzle 23, and an air outlet of the second air chamber 2 is connected to the second nozzle 25. The pressure regulating valve 13 includes a pressure regulating valve body and a pressure gauge 12. The solenoid valve 9 and the electrical proportional valve 6 are mounted on the middle partition plate 11.

The air compressor is connected to the pressure regulating valve 13 by means of a pipeline; the pressure regulating valve 13 is hermetically connected to the two-stage air filter 14 by means of threads; the two-stage air filter 14 is connected to the electric proportional valve 6 by means of a pipeline; the electrical proportional valve 6 is connected to the solenoid valve 9 by means of a pipeline; and the solenoid valve 9 is connected to the air chambers (the first air chamber 3 and the second air chamber 2) by means of a pipeline and an air path joint in sequence.

Figure 4A:
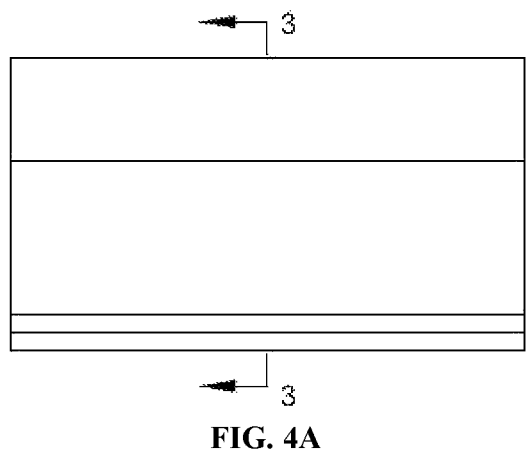
FIG. 4A is a front view of a first air chamber in the present disclosure.
Figure 4B:
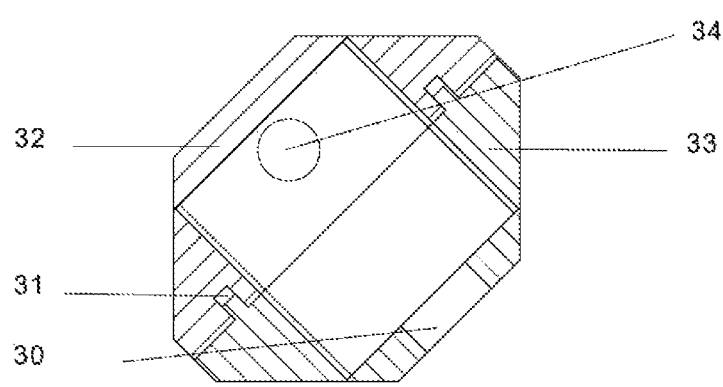
FIG. 4B is a sectional-structure schematic diagram of the first air chamber in the present disclosure.

In order to make the nozzle stable, make the air chamber convenient to mount and not obscure a shooting view of the camera 7, a housing of the first air chamber 3 is designed to be in a shape of an octagonal prism since under the condition that the air chamber is designed to be a conventional cube, a guide pipe of the nozzle has a turn and the nozzle will shake to influence a collection result. One surface of the octagonal prism of the first air chamber is fixed to a vertical surface of the L-shaped lifting table 24, and the first nozzle 23 is mounted on a surface adjacent to a lower side of a surface opposite the surface. Air flow entering the first nozzle 23 may be directly output from the air chamber to act on a surface of a viscoelastic material without shaking the air flow. As shown in FIGS. 4A-4B, the first air chamber 3 includes an air chamber upper portion 32 and an air chamber lower portion 33, the air chamber upper portion is connected to the air chamber lower portion by means of screws, a circle of sealing groove is provided in the air chamber upper portion 32, a circle of flange is arranged on the air chamber lower portion 33, and the flange is embedded into the sealing groove and abuts against a rubber gasket 31 preset in the sealing groove to achieve sealing so as to prevent air leakage; and an air inlet 34 is provided in a side surface of the air chamber upper portion 32, an air outlet 30 is provided in a bottom cover of the air chamber lower portion 33 and is in threaded connection to the first nozzle 23, and a joint is sealed by means of cold-setting adhesive. A side cover on the air chamber upper portion 32 is connected to a side plate of the L-shaped lifting table 24 by means of bolts, and the first nozzle 23 mounted on the bottom cover on the air chamber lower portion 33 inclines downwards to face a top surface of the second air chamber 2.

Figure 5:
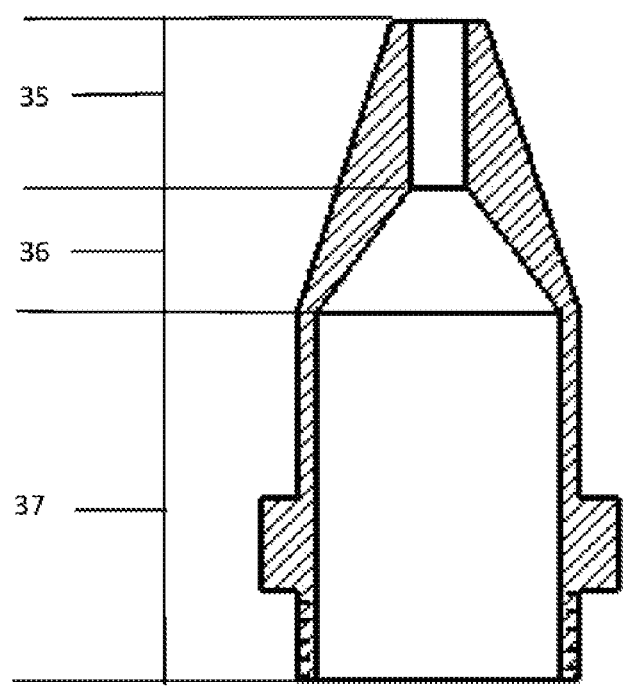
FIG. 5 is a sectional structural schematic diagram of a first nozzle.
Figure 6A:
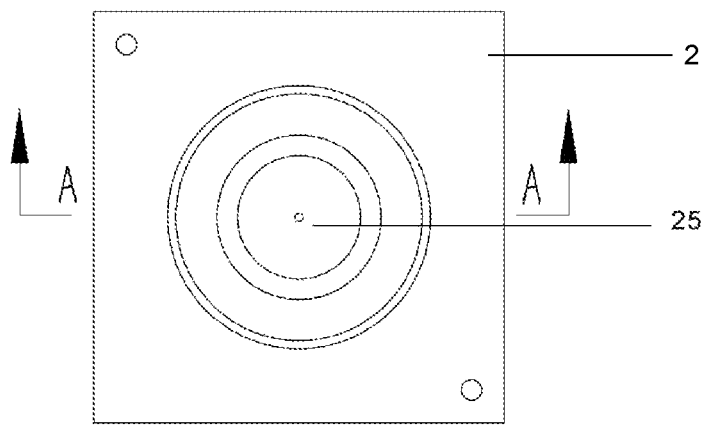
FIG. 6A is a top view of a second air chamber.
Figure 6B:
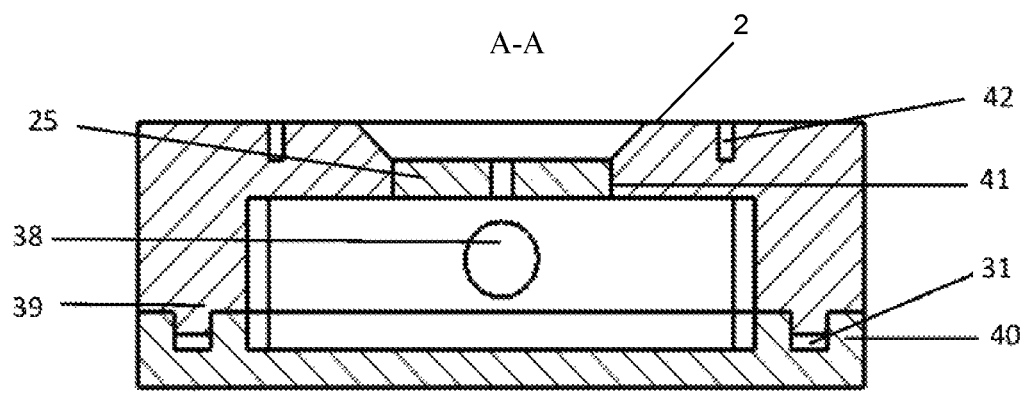
FIG. 6B is a sectional-structure schematic diagram of the second air chamber.
Figure 7A:
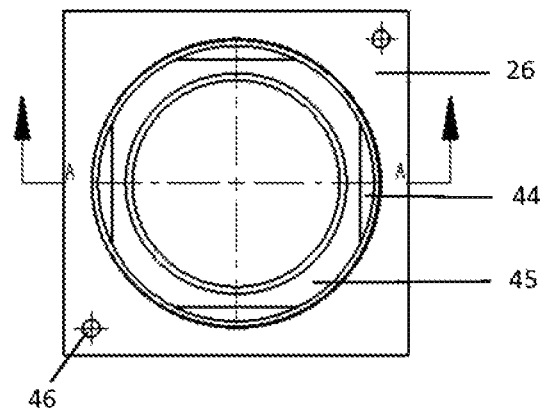
Figure 7B:
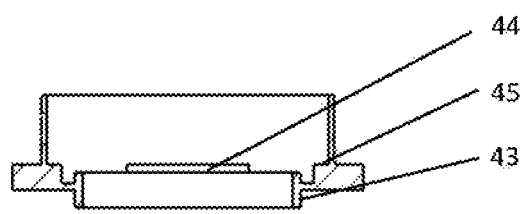
Figure 7C:
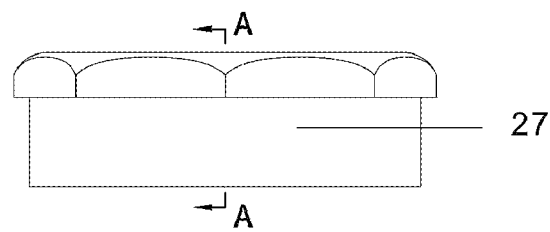
Figure 7D:
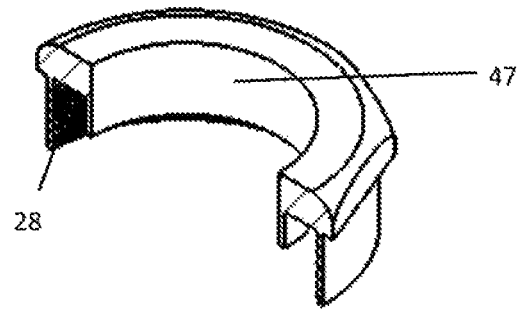
Figure 8A:
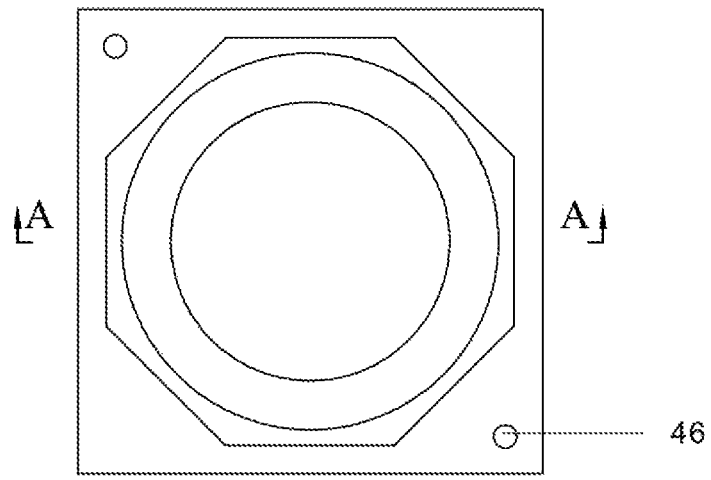
Figure 8B:
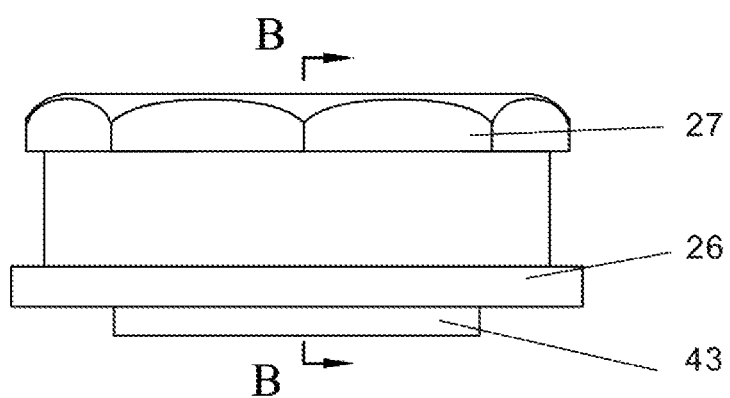
Figure 8C:
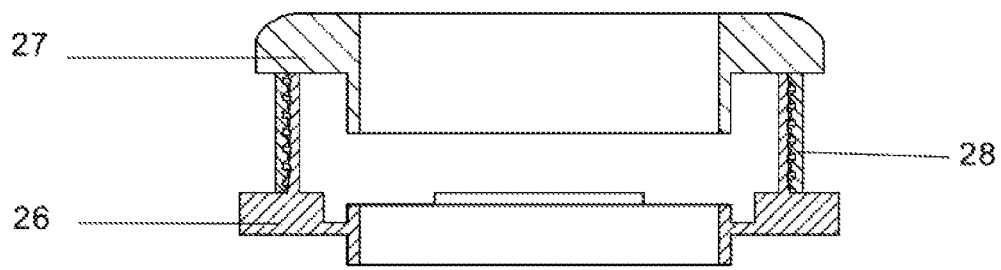
Figure 8D:
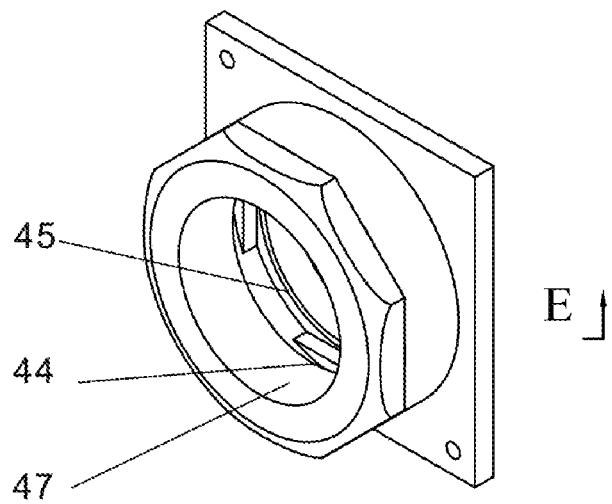
Figure 8E:
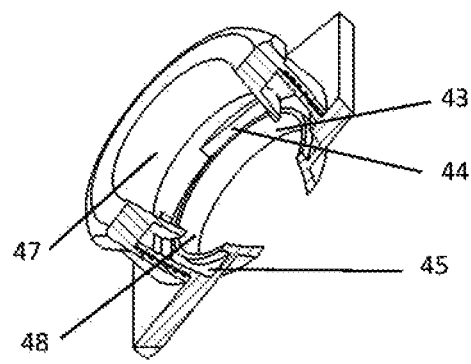
Figure 9A:
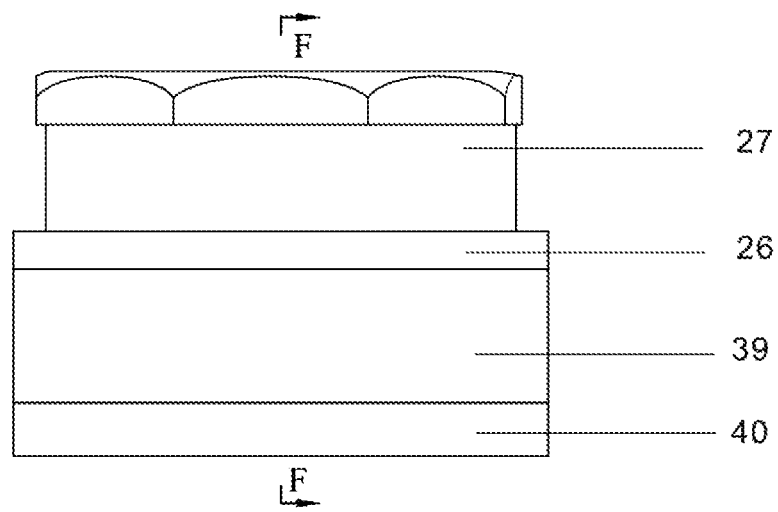
Figure 9B:
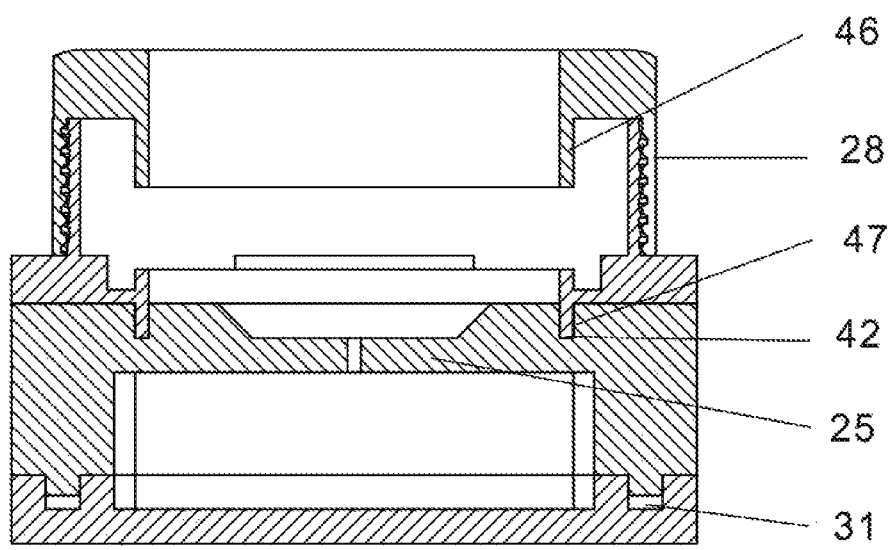

The first nozzle 23 is made of quartz stone with light transmittance not lower than 80%. As shown in FIG. 5, an inner cavity of the first nozzle 23 is provided with a connecting section 37, a converging section 36 and a diverting section 35 from top to bottom sequentially; an outer wall where the connecting section 37 is located is provided with external threads and is connected to a first air chamber main body by means of the threads, cold-setting adhesive seals a periphery of the connecting section of the nozzle, the connecting section 37 is cylindrical, the converging section 36 is conical and has an upper portion larger than a lower portion, the diverting section 35 is cylindrical, a length ratio of the converging section 36 to the diverting section 35 is not greater than 1:1.3, and a ratio of a length of the diverting section 35 to a diameter of an air outlet hole in the diverting section 35 is not less than 3:1; and the diameter of the air outlet hole in the diverting section 35 is not greater than 3 mm. The design of the first nozzle may minimize loss of the air flow in the nozzle, and may further make the air flow stably and uniformly act on the surface of the viscoelastic material. As shown in FIGS. 6A-6B, the second air chamber 2 has a cubic structure and is fixed to the bottom plate of the L-shaped lifting table 24 by means of a screw and a nut, the second air chamber 2 includes an air chamber upper portion 39 and an air chamber lower portion 40 from top to bottom sequentially, the air chamber upper portion 39 is connected to the air chamber lower portion 40 by means of screws, a circle of sealing groove is provided in the air chamber lower portion 40, a circle of flange is arranged on the air chamber upper portion 39, and the flange is embedded into the sealing groove and abuts against a rubber gasket 31 preset in the sealing groove to achieve sealing so as to prevent air leakage. The air inlet 38 is provided in a side surface of the air chamber upper portion 39, the air outlet 41 is provided in the middle of a top surface of the air chamber upper portion 39, the air outlet 41 is used for mounting the second nozzle 25, and the second nozzle 25 is cylindrical with a 3 mm diameter hole in the middle.

As shown in FIGS. 6A-6B, 7A-7D, 8A-8E, and 9A-9B, a circle of groove 42 and two threaded holes 46 are provided in the surface of the air chamber upper portion 39 of the second air chamber 2 for mounting and fixing a sample fixing clamp. The air inlet hole 38 is located on a side of the second air chamber upper portion, the air outlet 41 is located in a center of the air chamber upper portion 39, and the second nozzle 25 is mounted at the air outlet 41 and sealed with a sealant. The sample fixing clamp includes a base 26 and a pressing nut 27, a body of the base 26 is of a hollow cylinder shape, a lower portion of the body protrudes outwards to form a circle of flange 43, a threaded hole 46 is provided in the base 26 and connected to the threaded hole 46 of the second air chamber upper portion 39 by means of a screw, a portion 43, below the flange, of the body of the base 26 is embedded into the groove 42 in the surface of the second air chamber upper portion, an upper portion of the body of the base 26 is provided with external threads 28, the pressing nut 27 is provided with internal threads corresponding to the external threads, and the pressing nut 27 is connected to the base 26 by means of threads 28; and a circle of boss 45 is arranged on a lower portion in a cavity of the body of the base 26 for supporting a sample, four positioning plates 44 are arranged on an upper portion of the boss 45, the four positioning plates 44 are oppositely arranged pairwise, side edges, away from a cavity wall, of the positioning plates are straight edges, and the side edges between two opposite positioning plates are parallel to each other. The pressing nut 27 is a hollow nut, and an inner cavity of the pressing nut extends downwards to form a circle of rib 47 for fixing a viscoelastic sample 29 under the action of air pressure.

When fixing the sample, the pressing nut 27 is unscrewed, the sample 29 is laid flat on the boss 45. Under the condition that the sample is not circular, a straight edge of the sample may be aligned with a side edge of a pressing plate, so as to well position the sample, then the pressing nut 27 is tightened, and the rib 47 compresses the sample 29. Air pressure comes out of the second nozzle 25 to act on the sample 29 to form a protrusion on the surface of the sample under the action of the air pressure, or the air pressure comes out of the first nozzle 23 to act on the sample (29) to form a protrusion on the surface of the sample under the action of the air pressure.

The image collection system includes a camera 7 (an industrial two-dimensional camera or a three-dimensional structured light camera), an LED annular light source 5, a USB data transmission device and a light source controller. The camera 7 is located over the second air chamber 2 and connected to the computer, the annular light source 5 is arranged around the camera 7 (the three-dimensional structured light camera collects point cloud images without turning on the annular light source), and the annular light source 5 is connected to the middle partition plate 11 of the machine body by means of a screw.

The controlling and information processing system includes a mobile computer and an A/D conversion module 16, where the mobile computer is in serial port communication connection with the camera 7 by means of a network cable; the A/D conversion module 16 is connected to the two-position five-way double-head pneumatic solenoid valve 9 and is used for controlling on-off of air outlet joints, connected to the two air chambers respectively, of the two-position five-way double-head pneumatic solenoid valve 9; and the computer is connected to the A/D conversion module 16, and performs voltage control on the electrical proportional valve 6 by means of the A/D conversion module 16 so as to control an air flux entering the electrical proportional valve 6. In order to reduce an influence of an environment background on extraction of rheological process feature information of an image, the mobile computer calls an Opencv two-dimensional image processing library to perform background segmentation on the material sample image collected by the two-dimensional camera, and then extracts the rheological process feature information of the image subject to background segmentation.

A pressure gauge is arranged on the electrical proportional valve 6 and used for monitoring and displaying a value of air pressure entering the electrical proportional valve, a control voltage change of the electrical proportional valve falls within a range of 0 V-5 V, when the voltage changes from 0 V to 5 V, the air flux of the electrical proportional valve 6 is gradually increased, and the air pressure flowing out of the electrical proportional valve 6 is gradually increased from zero to 0.5 MPa. An inner diameter of an air inlet of the electric proportional valve is 10 mm.

A light source starting switch 21 is arranged on a front portion of the machine body, the LED annular light source 5 is connected to the light source controller, the light source controller is connected to a computer, so as to control brightness of a light source by means of the computer.

The air outlet holes of the two-position five-way double-head pneumatic solenoid valve 9 need to be controlled by an air pressure control system, so as to achieve conversion of the air flow sprayed from an upper surface of the viscoelastic material 29 to the air flow sprayed from a lower surface of the viscoelastic material 29 or conversion of the air flow sprayed from the lower surface of the viscoelastic material 29 to the air flow sprayed from the upper surface of the viscoelastic material 29, specifically, one air outlet hole is closed, and the other air outlet hole is used for air outlet. One air pressure injection mode may be automatically converted into another air pressure injection mode.

During work, the viscoelastic material 29 is cut into sheets of a fixed size, the pressing nut 27 is unscrewed to lay the sample 29 flat on the boss 45, and the pressing nut 27 is tightened to press the sample. Power switches 20 and 21 are turned on, a measuring system is started, a height of the L-shaped lifting table 24 is adjusted according to measuring requirements, air flow loading time and unloading time are set, a parameter of the two-dimensional camera are set and stored, and the air outlet hole of the two-position five-way double-head pneumatic solenoid valve 9 is controlled to achieve air pressure action from the upper surface or the lower surface of the viscoelastic material 29 (the first nozzle sprays air downwards or the second nozzle sprays air upwards); and the two-dimensional camera 7 collects continuous change images of a concave or convex process of the viscoelastic material 29 separately, the continuous change images are sent to the computer in real time, and the computer extracts five deformation features of the continuous change images by calling the OpenCV image processing system, and draws a deformation feature curve in real time by means of Qt Widgets for Technical Applications (QWT). After measurement, a reset button 22 is started, the whole measuring system is closed, and the lifting table is reset to an original height.

Since the air pressure acts on the surface of the material sample, a texture shape of the surface of the material may be changed over the acting time and mode of the air pressure, and texture features of the surfaces of different viscoelastic materials and viscoelastic materials with different qualities are different under the same air pressure. After receiving image data collected by the two-dimensional camera, the mobile computer executes the following steps:

step: 1. call an Opencv two-dimensional image processing library to preprocess an image; step 2. perform graying and gray level quantization processing on the image subject to background segmentation; step 3. select a parameter; and 4. extract a deformation feature of a rheological process in an image of a viscoelastic material sample.

Specifically, step 1. call an Opencv two-dimensional image processing library, perform binarization processing on the obtained image, perform negation operation to obtain a background segmented mask image, and finally use the mask to remove a viscoelastic material background by means of the following operational formula:

$$I_{mask}=I*I_{temp} \tag{1}$$

where in the formula, $I_{mask}$ is a background segmented image obtained by preprocessing, and $I_{temp}$ is a mask;

step 2. perform gray level processing on an RGB image of the viscoelastic material sample subject to background segmentation, and quantify the image at the gray level;

step 3. select parameters, specifically, (1) select, by taking a pixel point to be computed as a center, a size of a matrix to be computed; (2) set a distance between the selected pixel point and another point deviating from the selected pixel point as step distance d; and (3) select a direction $\varphi^{\circ}$; and step 4. extract a rheological process feature of the image of the viscoelastic material sample, where feature $f_1$ is used for representing similarity, in a transverse direction and a longitudinal direction, obtained after statistics is performed on the condition that two pixels which are kept at a certain distance in the image of the material sample have certain gray levels respectively;

feature $f_2$ is used for representing grooves on the surface of the image of the viscoelastic material, and the deeper the grooves are, the greater the value is;

feature $f_3$ is used for representing a uniformity degree of gray level distribution and a thickness degree of texture of the image of the viscoelastic material sample;

feature $f_4$ is used for representing local texture change between different regions of the image of the viscoelastic material sample, the larger the value is, the smaller the change of the surface wrinkle texture between different regions is, and vice versa; and feature $f_5$ is used for representing a degree of regularity of the texture of the surface of the viscoelastic material sample, the higher the regularity is, the smaller the value is, and vice versa.

Mathematical formulas for extracting the five deformation features ($f_1$, $f_2$, $f_3$, $f_4$, $f_5$) of the image of the viscoelastic sample material are as follows:

feature $f_1$:

$$f_1 = \frac{\sum_{i=0}^{N-1}\sum_{j=0}^{N-1}[i \times j \times p(i,j) - \mu_x \mu_y]}{\sigma_x^2 \sigma_y^2} \quad (2)$$

feature $f_2$:

$$f_2 = \sum_{i=0}^{N-1}\sum_{j=0}^{N-1}[(i-j)^2 p(i,j)] \quad (3)$$

feature $f_3$:

$$f_3 = \sum_{i=0}^{N-1}\sum_{j=0}^{N-1} p^2(i,j) \quad (4)$$

feature $f_4$:

$$f_4 = \sum_{i=0}^{N-1}\sum_{j=0}^{N-1} \frac{p(i,j)}{1+(i-j)^2} \quad (5)$$

feature $f_5$:

$$f_5 = -\sum_{i=1}^{N-1}\sum_{j=1}^{N-1} p(i,j) \log p(i,j) \quad (6)$$

in the formula $$\mu_x = \sum_{i=0}^{N-1} i \sum_{j=0}^{N-1} p(i,j); \mu_y = \sum_{i=0}^{N-1} j \sum_{j=0}^{N-1} p(i,j);$$

$$\sigma_x^2 = \sum_{i=0}^{N-1}(i-\mu_x)^2 \sum_{j=0}^{N-1} p(i,j); \sigma_y^2 = \sum_{i=0}^{N-1}(i-\mu_y)^2 \sum_{j=0}^{N-1} p(i,j)$$

in the formula:

$$p(i,j) = \frac{p_{ij}}{\sum_{i=0}^{N-1}\sum_{j=0}^{N-1} p_{ij}};$$

p in the formula is an N*N two-dimensional matrix; p (i, j) is a probability of co-occurrence of two gray values i and j of a reference point (x, y) and an offset point (x+d, y+d), with a given distance d and a given direction $\varphi^0$, on a straight line with a direction $\varphi^0$, the gray value of the reference point (x, y) is i, and the gray value of the offset point (x+d, y+d) is j; $p_{ij}$ is the number of times that a reference gray pixel value i appears in a pixel pair with a gray pixel value j with a distance d and a direction $\varphi^0$; N is a gray level of one image; and x and y are horizontal axis coordinates of the pixel point respectively.

Dimensions of the extracted five surface deformation descriptors are different, such that data dimension normalization preprocessing needs to be performed on the five surface deformation descriptors subsequently, and the used formula is shown in the following.

$$X = \frac{(x - x_{min})}{(x_{max} - x_{min})}$$

x in the formula is a certain deformation feature value extracted by image processing and may be features $f_1$, $f_2$, $f_3$, $f_4$, and $f_5$; $x_{min}$ is a minimum value of the deformation feature values extracted by image processing; $x_{max}$ is a maximum value of the deformation feature values extracted by image processing; and X is a feature value finally input into a quality detection discrimination model.

Therefore, specific air pressure acts on the surface of the viscoelastic material to change texture wrinkles on the surface of the viscoelastic material, and by extracting deformation features of the surface of the material, five texture feature-time change curves are drawn by means of QWT. Feature values obtained from recesses and protrusions formed on the surface of the viscoelastic material in different air pressure action modes (air pressure action on the upper surface of the viscoelastic material and air pressure action on the lower surface of the viscoelastic material) under the same air pressure action are analyzed, and curves of slow concave and convex processes of the surface are drawn.

The two-dimensional camera in the above implementation mode collects a two-dimensional image, the industrial camera 7 in the image collection system may also be replaced by a three-dimensional structured light 3D camera, and other structures are not changed. In this way, the detection system may analyze the processes of concave and convex deformation formed on the surface of the viscoelastic material under different air pressure action modes (air pressure action on an upper surface of food or air pressure action on a lower surface of food) under the same constant air pressure action, and extracts features from the deformation information to serve as indexes for quality detection of the viscoelastic material.

During work, the viscoelastic material 29 is cut into sheets of a fixed size, the pressing nut 27 is unscrewed to lay the sample 29 flat on the boss 45, and the pressing nut 27 is tightened to press the sample. Power switches 20 and 21 are turned on, a measuring system is started, a height of the L-shaped lifting table 24 is adjusted according to measuring requirements, air flow loading time and unloading time are set, a parameter of the camera 7 are set and stored, the air outlet hole of the two-position five-way double-head pneumatic solenoid valve 9 is controlled to achieve air pressure action from the upper surface or the lower surface of the viscoelastic material 29 (the first nozzle sprays air downwards or the second nozzle sprays air upwards), the surface of the viscoelastic material 29 to be measured is subject to constant air force from the first nozzle or the second nozzle, and when the action keeping time of the constant air force reaches a triggering shooting time (a moment when the food has maximum deformation quantity under the air force action) set by the camera 7, the three-dimensional structured light 3D camera 7 is triggered to shoot a three-dimensional structure deformation image of the viscoelastic material 29 to be measured. After reaching the air force constant action time, the air force is unloaded, and after the viscoelastic material 29 to be measured is no longer pressed, the deformation is recovered. The images collected by the camera 7 are transmitted to the mobile computer by means of serial communication for storage and processing.

The mobile computer calls a point cloud processing library (PCL), and performs extraction and display of feature information of three-dimensional structural deformation on an obtained point cloud image, Specifically, the steps are as follows:

(1) extract a plane projection area of a deformation convex or concave region of a three-dimensional structure, firstly extract an interested region of obtained deformation convex or concave point cloud of viscoelastic food, perform filtering and noise reduction and downsampling processing to reduce noise and a data size of the point cloud so as to obtain a deformed overall contour, project point cloud data subject to downsampling processing to plane XOY, plane XOZ and plane YOZ, divide three adjacent points into a triangle in three coordinate planes respectively to establish a triangle patch index, and traverse and respectively accumulate and compute areas $S_{xoy}$, $S_{xoz}$, and $S_{yoz}$ projected to plane XOY, plane XOZ and plane YOZ, where $$S_{xoy}, S_{xoz}, S_{yoz} = \sum_{i=0}^{n} S_i, \tag{1}$$

where:

$S_i$ is an area of each projected triangle on the plane, and is computed by means of a formula:

$$S_i = \sqrt{l_i(l_i-a_i)(l_i-b_i)(l_i-c_i)} \tag{2}$$

where i refers to a patch index number, $l_i$, refers to ½ of a perimeter of the triangle, $a_i$, $b_i$, and $c_i$ refer to side lengths of the triangle, and n refers to a total patch number;

(2) extract a volume of the deformation convex or concave region of the three-dimensional structure, firstly project obtained deformation convex or concave point cloud to plane XOY, perform mesh division on plane points by means of cubic spline interpolation processing, compute an average value hi of a difference between an area of each mesh and an elevation parameter of an original point cloud, and traverse the entire plane, and perform accumulation to obtain a volume V of the concave deformation region, that is, $$V = \sum_{i=0}^{n} S_i h_i; \tag{3}$$

(3) compute an area of a triangular mesh curved surface of the deformation convex or concave region (a surface area of the convex or concave region) of the three-dimensional structure, specifically, perform curved surface interpolation fitting on obtained deformation convex or concave region point cloud, remove discrete points, select a sample triangular patch from uniformly distributed scattered points subject to downsampling processing as an initial curved surface, take the triangular patch as a space region growth point, continuously extend a boundary of the curved surface around to finally form a complete triangular mesh curved surface, and obtain a triangular mesh curved surface model according to a topological connection relation of three points in the plane; where each patch includes an index of the original point cloud, the entire curved surface mesh is traversed, and the areas of the triangles are accumulated to obtain a point cloud area Sb of a space viscoelastic sample, $$S_b = \sum_{j=0}^{n} s_j, \tag{4}$$

where j refers to a patch index number, $s_j$ refers to a triangle area (computed in the same way as formula 2), and n refers to a total patch number; and (4) extract a height or depth of the deformation convex or concave region of the three-dimensional structure, use a minimum bounding box algorithm to enclose all scattered points of the deformation convex or concave region of the three-dimensional structure into a minimum cuboid, where the minimum cuboid has a minimum volume, and obtain eight vertex coordinates of a bounding box of the minimum cuboid by means of computation, where the height or depth H of the deformed region is a vertical distance of the bounding box and may be expressed as:

$$H=\sqrt{(x_1-x_5)^2+(y_1-y_5)^2+(z_1-z_5)^2}$$

where $x_1$, $y_1$, and $z_1$ are coordinates of a first vertex of an upper plane of the bounding box, $x_5$, $y_5$, and $z_5$ are coordinates of a fifth vertex of a lower plane of the bounding box, and the first vertex and a second vertex are located on one edge.

Based on the above technical solution, according to a point cloud rheological image obtained based on a creep property of the viscoelastic material, three plane projection areas of a deformation convex or concave region of a three-dimensional structure of the viscoelastic material over time, a volume of the deformation convex or concave region of the three-dimensional structure, a triangular mesh curved surface area of the deformation convex or concave region (the surface area of the convex or concave region) of the three-dimensional structure, and a height or depth of the convex or concave region are obtained, and six time-deformation curves of the food are drawn. The correlation analysis and comparison of these features are performed to find out a feature having greater correlation of food rheology based on the creep property of food so as to input the feature into a viscoelastic food quality detection model.

By means of the present disclosure, it is possible to reflect a rheological process of a viscoelastic material as a whole, rather than measuring a rheological process only at a certain point by a single point laser; a deformation feature extraction algorithm is used to extract feature information in the rheological process of the viscoelastic material, so as to improve accuracy of a detection system for viscoelastic material quality detection; the present disclosure may use different air pressure action modes (air pressure action on an upper surface of the viscoelastic material and air pressure action on a lower surface of the viscoelastic material) to act on the surface of the viscoelastic material, and continuously collect a concave creep process and a convex creep process of the viscoelastic material by means of machine vision; and any air pressure action mode (air pressure action on the upper surface of the viscoelastic material or air pressure action on the lower surface of the viscoelastic material) of the present disclosure alone may be an air pressure-machine vision based system for measuring a rheological property of a viscoelastic material.

What is claimed is:

1. An air pressure-machine vision based system for measuring a rheological property of a viscoelastic material, comprising:
    a machine body,
    a lifting experiment table system,
    an air pressure generation control system,
    an image collection system, and
    a controlling and information processing system,
    wherein the lifting experiment table system, the air pressure generation control system, the image collection system, and the controlling and information processing system are mounted on the machine body;
    wherein the lifting experiment table system comprises:
        a lifting table stepping motor,
        an L-shaped lifting table, and
        a lifting table motor driver,
        wherein the lifting table motor driver is connected to an L-shaped lifting table stepping motor and is configured to drive the lifting table stepping motor; and
        wherein the lifting table stepping motor is connected to the L-shaped lifting table and is configured to control lifting of the L-shaped lifting table;
    wherein the air pressure generation control system comprises:
        an air compressor,
        a pressure regulating valve,
        a two-stage air filter,
        an electrical proportional valve,
        a two-position five-way double-head pneumatic solenoid valve,
        a first air chamber, and
        a second air chamber,
        wherein the first air chamber and the second air chamber are mounted on the L-shaped lifting table separately, the first air chamber is mounted on a vertical plate of the L-shaped lifting table, the second air chamber is mounted on a bottom plate of the L-shaped lifting table, and the first air chamber is mounted above the second air chamber;
    wherein the first air chamber has a shape of an octagonal prism, a first surface of the octagonal prism is fixed to a vertical surface of the L-shaped lifting table, a first nozzle is mounted on a second surface of the octagonal prism, the second surface of the octagonal prism is adjacent to a third surface of the octagonal prism, the third surface of the octagonal prism is opposite to the first surface of the octagonal prism, and the second surface of the octagonal prism is under the third surface of the octagonal prism;
    wherein the first air chamber comprises a first air chamber upper portion and a first air chamber lower portion, the first air chamber upper portion is connected to the first air chamber lower portion by first screws, a circle of first sealing groove is provided in the first air chamber upper portion, a circle of first flange is provided on the first air chamber lower portion, and the circle of first flange is embedded into the circle of first sealing groove and abuts against a first rubber gasket preset in the circle of first sealing groove to achieve a sealing to avoid an air leakage;
    wherein a first air inlet is provided in a side surface of the first air chamber upper portion, a first air outlet is provided in a bottom cover of the first air chamber lower portion, the first air outlet is in a threaded connection to the first nozzle, and a joint of the threaded connection is sealed with a cold-setting adhesive;
    wherein the second air chamber has a cubic structure, a lower portion of the second air chamber is fixed to the bottom plate of the L-shaped lifting table by second screws, the second air chamber comprises a second air chamber upper portion and a second air chamber lower portion from top to bottom sequentially, the second air chamber upper portion is connected to the second air chamber lower portion by third screws, a circle of second sealing groove is provided in the second air chamber lower portion, a circle of second flange is provided on the second air chamber upper portion, and the circle of second flange is embedded into the circle of second sealing groove and abuts against a second rubber gasket preset in the circle of second sealing groove; and
    wherein a second air inlet is provided in a side surface of the second air chamber upper portion, a second air outlet is provided in a middle of a top surface of the second air chamber upper portion and used for mounting a second nozzle, and a groove and a threaded hole are provided in a surface of the second air chamber upper portion for mounting and fixing a sample fixture.

2. The air pressure-machine vision based system for measuring the rheological property of the viscoelastic material according to claim 1, wherein an air outlet of the air compressor is connected to an air inlet of the pressure regulating valve.

* * * * *